US006057163A

United States Patent [19]
McMillan

[11] Patent Number: 6,057,163
[45] Date of Patent: May 2, 2000

[54] LUMINESCENCE AND FLUORESCENCE QUANTITATION SYSTEM

[75] Inventor: Jeffrey Martin McMillan, Morgan Hill, Calif.

[73] Assignee: Turner Designs, Sunnyvale, Calif.

[21] Appl. No.: 09/067,610

[22] Filed: Apr. 28, 1998

[51] Int. Cl.$^7$ .................................................. G01N 21/76
[52] U.S. Cl. ...................................... 436/172; 422/82.08
[58] Field of Search .................................. 422/62, 63, 65, 422/82.05, 82.07, 82.08, 102, 103, 104; 436/46, 47, 164, 172

[56] References Cited

U.S. PATENT DOCUMENTS

| | | |
|---|---|---|
| 4,710,031 | 12/1987 | Kelly et al. . |
| 4,922,092 | 5/1990 | Rushbrooke et al. . |
| 5,048,957 | 9/1991 | Berthold et al. . |
| 5,202,091 | 4/1993 | Lisenbee . |
| 5,290,513 | 3/1994 | Berthold et al. . |
| 5,294,795 | 3/1994 | Lehtinen et al. . |
| 5,298,753 | 3/1994 | Sonne et al. . |
| 5,306,914 | 4/1994 | Yrjonen et al. . |
| 5,329,123 | 7/1994 | Oikari et al. . |
| 5,342,581 | 8/1994 | Sanadi . |
| 5,401,465 | 3/1995 | Smethers et al. . |
| 5,610,883 | 3/1997 | Yanagawa . |
| 5,611,994 | 3/1997 | Bailey et al. . |

OTHER PUBLICATIONS

Gerard N. Skews, "Advanced Imaging Analyzes Electrophoresis Gels", *Biophotonics International*, Electrophoresis Imaging, Sep./Oct. 1997 pp. 46–49.

P.H. Jago, et al., "An Evaluation of the Performance of Ten Commercial Luminometers", *Journal of Bioluminescence and Chemiluminescence*, vol. 3, Apr. 1989, pp. 131–145.

Haggart, R. et al., "The Photometric Properties of Cooled Slow–Scan Charge Coupled Devices as Detectors in Systems for Luminogenic Assays", *Journal of Bioluminescence and Chemiluminescence* (1990), pp. 365–368.

Hooper, Claire E., et al., "Quantitative Photon Imaging in the Life Sciences Using Intensified CCD Cameras", *Journal of Bioluminescence and Chemiluminescence* (1990), pp. 337–344.

Brauer, Reinhard, et al., "Measuring Luminescence with a Low Light–Level Imaging System Using Electronic Light Standards", *Journal of Bioluminescence and Chemiluminescence* (1993), pp. 13–17.

(List continued on next page.)

Primary Examiner—Elizabeth McKane
Assistant Examiner—Jennifer McNeil
Attorney, Agent, or Firm—Flehr Hohbach Test Albritton & Herbert LLP

[57] ABSTRACT

A sample reading apparatus and method. The apparatus includes a detection system for reading samples, a sample carrier support for holding a sample carrier in position for reading by the detection system, and a mask configured to expose selected portions of the sample carrier while covering other portions of the sample carrier such that the detection system reads the exposed portions of the sample carrier. At least one of the sample carrier and mask are movable to expose different portions of the sample carrier while covering other portions of the sample carrier. The method includes positioning a sample carrier on a support, obstructing a surface of the sample carrier with a mask which exposes selected portions of the sample carrier while covering other portions of the sample carrier, activating a detection system to read the contents of the portions of the sample carrier exposed by the mask, producing relative motion of the sample carrier and the mask to expose different portions of the sample carrier while covering other portions of the sample carrier including the previously exposed portions of the sample carrier, and activating a detection system to read the contents of the different portions of the sample carrier exposed by the mask.

27 Claims, 4 Drawing Sheets

OTHER PUBLICATIONS

Hooper, C.E., et al., "Measurement and Analysis of Chemiluminescent Protein and DNA Blots Using Photon Imaging with an Intensified CCD Camera", *Journal of Bioluminescence and Chemiluminescence* (1993), pp. 23–27.

Alton, G., et al., "Evaluation of a Versatile Imaging Camera Apparatus for Chemiluminescent ELISA and Monitoring Bacterial Bioluminescence", *Journal of Bioluminescence and Chemiluminescence* (1993), pp. 3–7.

Rushbrooke, J.G., et al., Luminescence Imaging in the Life Sciences Using an Intensified CCD System, *Journal of Bioluminescence and Chemiluminescence* (1993), pp. 28–32.

Wick, Robert A., et al., "A Comparison of Cooled CCD and Intensified CCD Detectors for luminescence Imaging", *Journal of Bioluminescence and Chemiluminescence* (1993), pp. 47–51.

Bernroider, G., et al., "Imaging Receptor Binding by Luminescence", *Journal of Bioluminescence and Chemiluminescence* (1993), pp. 8–12.

Berthold, F., et al., "An Imaging System for Bio–and Chemiluminescence, Fluorescence, ad Radioactivity", *Journal of Bioluminescence and Chemiluminescence* (1994), pp. 617–620.

Schoenfelner, B., et al., "The Lumigen CCD Camera System: An Economical Cooled CCD Camera System for Chemiluminescent Applications", *Journal of Bioluminescence and Chemiluminescence* (1994), pp. 633–636.

Mayerhofer, R., et al., "Visualization of Light Emission from Different Luciferases in Transgenic Organisms", *Journal of Bioluminescence and Chemiluminescence* (1994), pp. 607–611.

Ingle, M., et al., "Photon Counting Systems for Bioluminescence Imaging", *Journal of Bioluminescence and Chemiluminescence* (1994), pp. 637–640.

Fullam, PS, et al., "Comparison of Real Life Luminometer Sensitivity as Determined with Actual Luminescence Assays", *Journal of Bioluminescence and Chemiluminescence* (1996 pp. 553–556.

Mockel, B., et al., "The Night Owl Molecular Light Imager—a Low–Light Imaging System for Bio–and Chemiluminescence and Fluorescence", *Journal of Bioluminescence and Chemiluminescence* (1996), pp. 539–542.

Gutekunst, M., et al., The Lumi–Imager™, a Sensitive and Versatile System for Imaging, Analysis and Quantitation of Chemiluminescence on Blots and in Microtiterplates, *Journal of Bioluminescence and Chemiluminescence* (1996), pp. 543–544.

Contag, Christopher H., et al., "Visualizing Gene Expression in Living Mammals Using a Bioluminescent Reporter", *Photochemistry and Photobiology*, 1997, 66(4), pp. 523–531.

Astromed Limited Brochure, "Astromed Ultra low light level imaging systems", Astromed Limited, Cambridge, England.

EG&G Berthold Brochure, "Luminograph LB 980", EG&G Berthold, Bad Wildbad, Germany.

Hamamatsu Brochure, "ARGUS–50 Series", Hamamatsu Photonics, Hamamatsu, Japan.

Image Research Brochure, "BIQ The Biomedical Image Quantifier", Image Research, Cambridge, England.

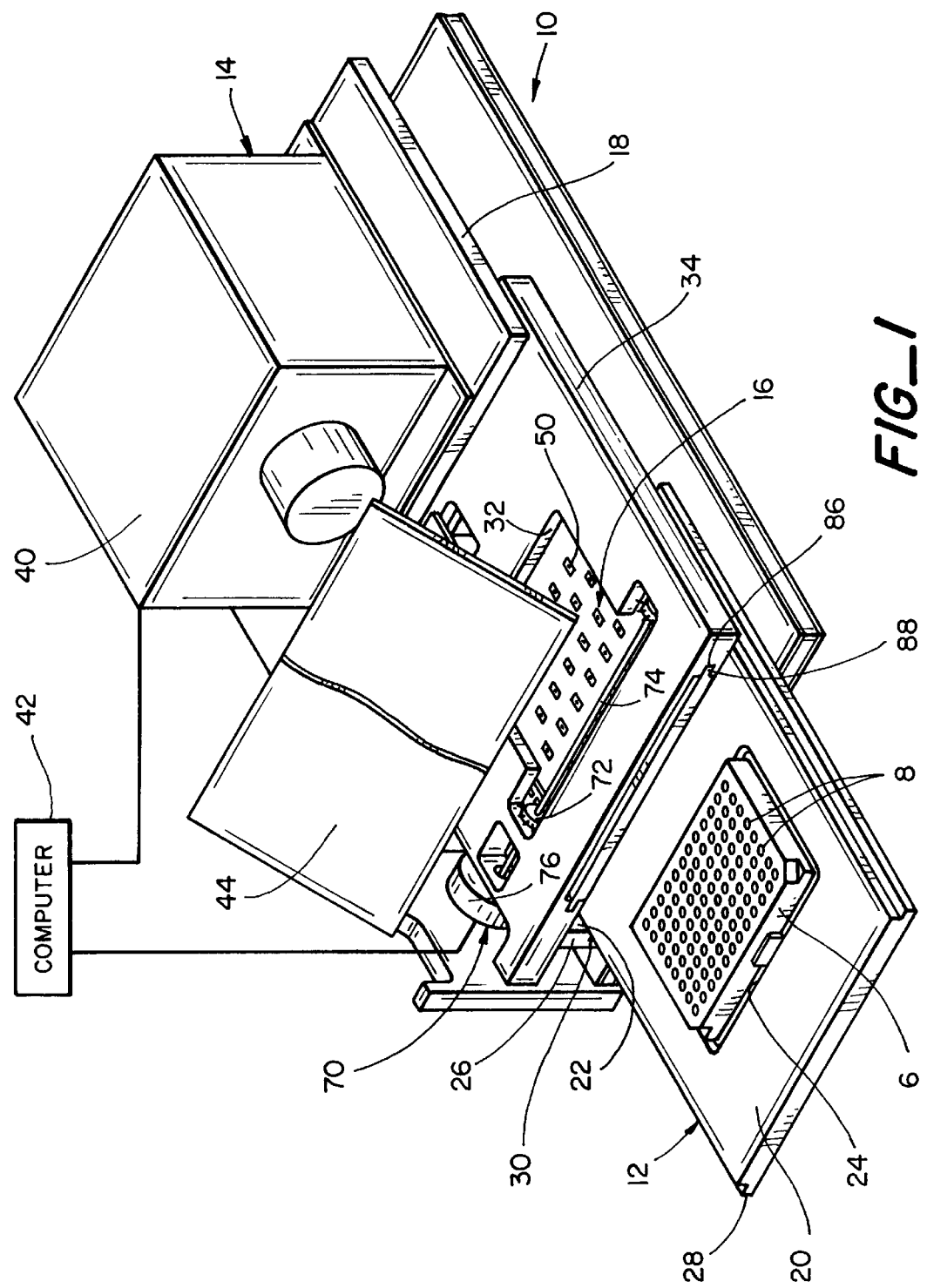

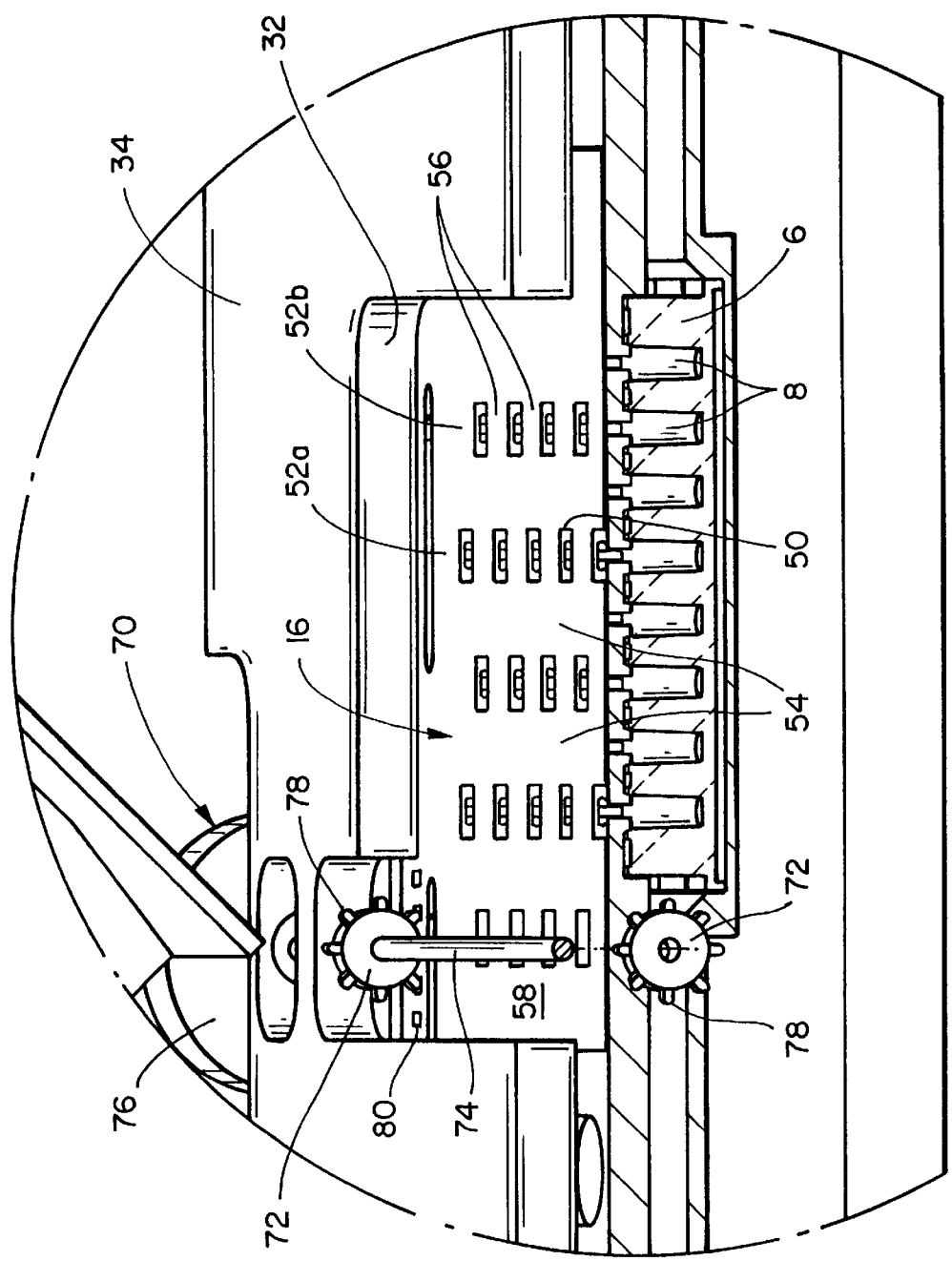
FIG_2

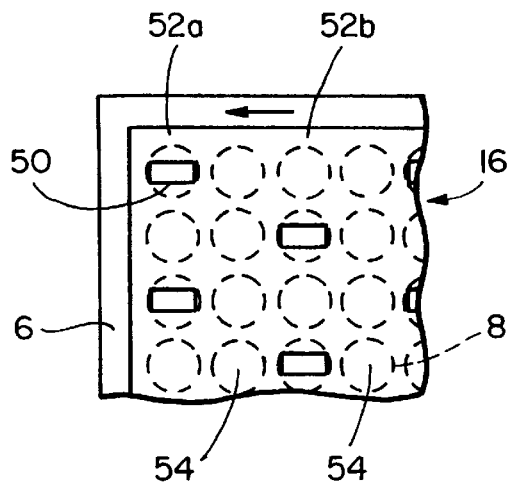
FIG_3A
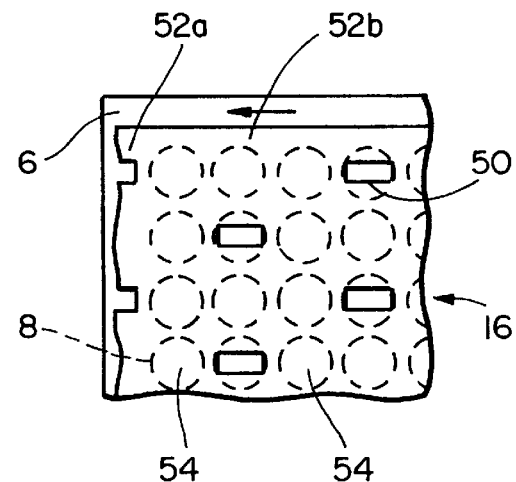
FIG_3B
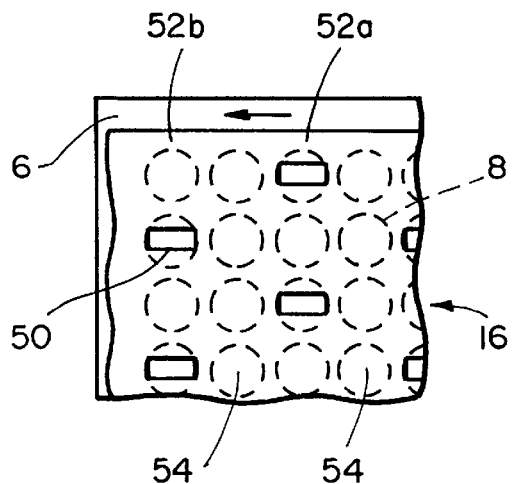
FIG_3C
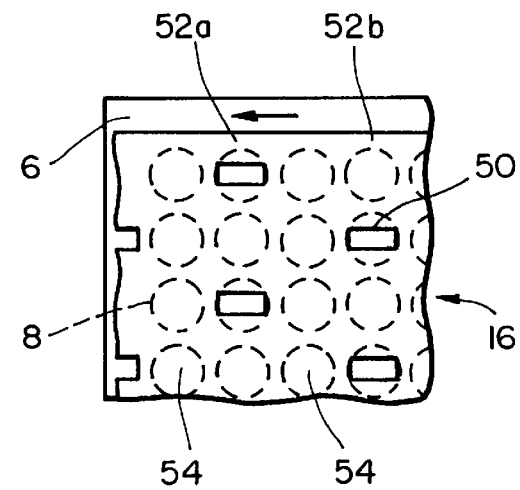
FIG_3D

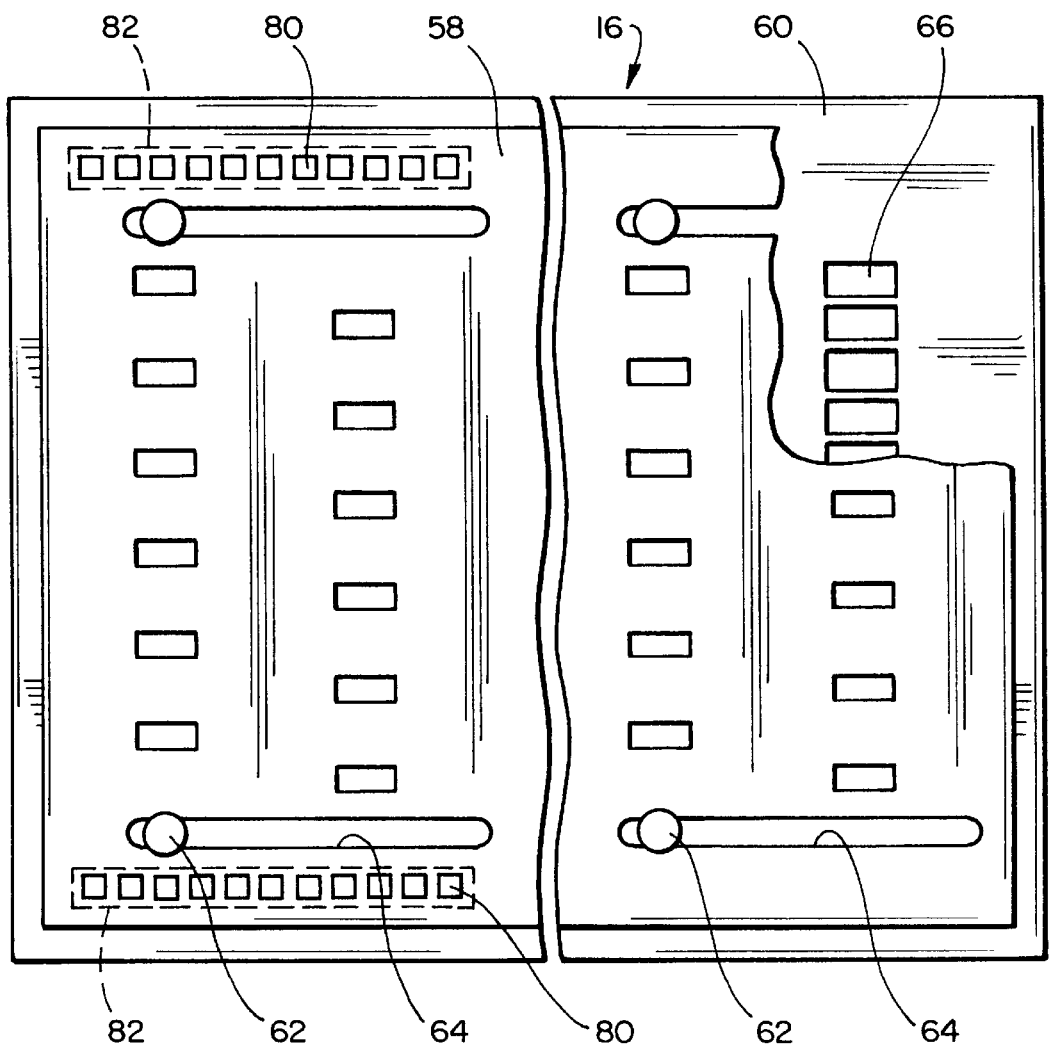
FIG_4

LUMINESCENCE AND FLUORESCENCE QUANTITATION SYSTEM

BRIEF DESCRIPTION OF THE INVENTION

This invention relates in general to a system for reading samples and, more particularly, to a system for quantitating light emitted from a sample.

BACKGROUND OF THE INVENTION

The quantitation of light emitted by a sample, such as by luminescence or fluorescence, provides a useful method of analyzing a sample under a wide range of applications. Examples of applications where the emitted light may be used to analyze the sample include, but are not limited to, genetic reporting, enzyme assays, immunoassays, the quantitation of DNA proteins, detection of antigens, and the identification of a sample or the composition of a sample. Luminescence and fluorescence assays, including bioluminescence and chemiluminescence, are extremely sensitive such that any stray light intercepted by the detection system may have a significant impact upon the results. Thus, a system for accurately, consistently and reliably measuring the amount of light emitted from a sample is desirable.

Luminescence assays and the like are often conducted using a sample tray such as a microwell plate which holds a plurality of samples for increased throughput. With the microwell plate and the like, samples are retained in a plurality of closely spaced wells formed in the plate. The samples in the nearby wells provide a source of stray light which, given the sensitivity of the assays, may interfere with the ability to accurately quantitate the light emitted from a selected sample. This crosstalk phenomena is particularly damaging to the assay results when a sample exhibiting low luminescence is located in the vicinity of a sample with high luminescence, with the bright sample essentially preventing any meaningful reading of the adjacent low-light sample.

One method of reading a sample plate utilizes a photodetector which reads one sample well at a time, with the photodetector and/or the sample tray being moved to successively align the photodetector with each of the wells in the plate. U.S. Pat. No. 5,202,091 shows an example of a system in which the tray is moved to align individual wells with an aperture formed in a top plate of the sample chamber. The photodetector reads the sample through the aperture in the top plate. Since only the selected well is visible, the top plate may reduce crosstalk interference from the adjacent wells. However, moving the tray to precisely align each well with the aperture is complicated and time consuming. Moreover, sample luminescent intensity can change over time. Because of the amount of time required to individually read the samples, accurate measurements of the later samples may not be obtained because of sample decay over time.

U.S. Pat. No. 5,290,513 shows a system in which the tray is moved back and forth in one direction and the photodetector is moved back and forth in a direction perpendicular to the motion of the tray. Although the movement of the tray is simplified compared to the system of U.S. Pat. No. 5,202,091, requiring movement of both the tray and the photodetector increases the complexity of the system. U.S. Pat. No. 5,401,465 shows another example of a system in which the sample tray is moved relative to the photodetector. The photodetector is biased by springs against the sample tray to close the gap between the upper edges of the wells and the aperture of the photodetector.

In the system shown in U.S. Pat. No. 5,202,091, the tray is held within a box-like holder. The top of the holder is a mask plate formed with a plurality of apertures. Each of the wells in the sample tray is aligned with one of the apertures in the mask plate to expose the samples retained within the tray holder. The mask plate provides a means of viewing the samples enclosed within the tray holder, but does not eliminate crosstalk effects since every well is exposed through the plate. U.S. Pat. No. 5,611,994 shows another example of a system in which the tray holder is moved relative to a fixed optical system. The tray holder includes a top mask plate which is pivotally mounted to the body of the tray holder, with apertures in the mask plate being aligned with each of the sample wells in the tray. The tray of the system shown in U.S. Pat. No. 5,290,513 is pressed against a diaphragm plate to reduce crosstalk effects between adjacent sample containers. The stationary diaphragm plate is formed with a row of holes which are aligned with one row of sample containers in the tray. The photodetector reads the samples through the holes in the diaphragm plate. Since an entire row of sample containers are exposed through the diaphragm plate, the adjacent samples may interfere with the reading. A system for quantitating light emitted from a plurality of samples which minimizes or eliminates crosstalk between adjacent samples is desirable.

U.S. Pat. No. 4,710,031 shows an example of a microwell plate reader which includes a light source positioned below the microwell plate for illuminating the wells. A transparent overlay with a plurality of black dots is positioned between the light source and the plate. A first reading of the sample is made when the transparent sections of the overlay between the black dots are aligned with the wells so that the light source illuminates the samples. For the second reading, the samples are viewed against a black background provided by moving the overlay to align a black dot with each well. The system may be used to examine the precipitates or suspended material of a sample in front of a black background using side lighting, and then to examine the colors of the samples by illuminated the samples from below.

A system for the efficient measurement of light emitted by a plurality of samples is desirable. A quantitation system which minimizes or eliminates crosstalk effects is also desirable. Similarly, a quantitation system which may be easily and inexpensively manufactured and maintained and efficiently operated to consistently achieve reliable results is desirable.

OBJECTS AND SUMMARY OF THE INVENTION

It is a primary object of the present invention to provide a quantitation system for detecting the amount of light emitted by a plurality of samples.

It is a further object of the present invention to provide a quantitation system for simultaneously reading a wide range of sample intensities.

It is another object of the present invention to provide a quantitation system for minimizing crosstalk effects from nearby samples.

It is still another object of the present invention to provide a system for rapidly and reliably reading a plurality of samples.

A more general object of the present invention is to provide a quantitation system which may be easily and inexpensively manufactured and maintained. Another general object of this invention is to provide a quantitation system which is simple to use.

In summary, this invention provides a sample reading system which is particularly suitable for quantitation of the light emitted by the sample. The sample reading apparatus generally includes a detection system for reading samples, a sample carrier support and a mask. The sample carrier support holds a sample carrier containing one or more samples in position for reading by the detection system. The mask is configured to expose selected portions of the sample carrier while covering other portions of the sample carrier such that the detection system reads the exposed portions of the sample carrier. The mask is repeatedly adjustable to expose different portions of the sample carrier while covering other portions of the sample carrier.

The method of the invention includes positioning a sample carrier on a support and adjusting a mask to expose selected portions of the sample carrier while covering other portions of the sample carrier. A detection system is activated to read the contents of the portions of the sample carrier exposed by the mask. The method also includes adjusting the mask to expose different portions of the sample carrier while covering other portions of the sample carrier, including the portions of the sample carrier which were previously exposed by the mask. The detection system is activated again to read the contents of the portions of the sample carrier exposed by the mask.

Additional objects and features of the invention will be more readily apparent from the following detailed description and appended claims when taken in conjunction with the drawings.

BRIEF DESCRIPTION OF THE DRAWINGS

FIG. 1 is a pictorial view, partially broken away, of a quantitation system in accordance with this invention.

FIG. 2 is an enlarged, pictorial view, partially broken away, of the quantitation system of FIG. 1.

FIGS. 3A–3D schematically illustrate the mask of FIG. 1 and a sample tray, showing the mask in different positions relative to the sample tray.

FIG. 4 is an enlarged view of the mask of FIG. 1.

DETAILED DESCRIPTION OF THE INVENTION

Reference is now made in detail to the preferred embodiment of the invention, which is illustrated in the accompanying figures. Turning now to the drawings, wherein like components are designated by like reference numerals throughout the various figures, attention is directed to FIG. 1.

FIG. 1 shows a quantitation system 10 in accordance with this invention which is particularly suitable for rapidly and reliably reading a plurality of samples. The quantitation system generally includes a sample holder 12, a detection system 14, and a mask assembly 16 positioned between the samples and the detection system 14. The frame 18 of the quantitation system supports the components of the system including the detection system 14. Thus, alignment of the detection system 14 relative to the sample holder 12 may be precisely controlled and transport and storage of the system is facilitated. However, it is to be understood that in other modifications of the invention the detection system 14 may be separate from the frame 18.

The configuration of the sample holder 12 is subject to considerable variation. In the illustrated embodiment, the sample holder 12 includes a shelf 20 which supports a sample tray such as microwell plate 6 in a sample chamber 22 of the frame 18. As is well known, the microwell plate 6 typically includes a plurality of wells 8 arranged in a rectangular array. The illustrated microwell plate 6 includes 96 wells arranged in an 8×12 array. Other microwell plates having a greater or lesser number of wells or a different array configuration are available in the art for holding a plurality of samples. It is to be understood that the microwell plates of any configuration as well as other types of devices for holding one or more samples may be used with the quantitation system 10 of this invention. In the illustrated embodiment, the microwell plate 6 is seated in a recessed area 24 of the shelf 20 to ensure the accurate placement of the plate 6 within the sample chamber inside of the frame 18. Thus, the recessed area 24 closely follows the shape of the microwell plate 6. Instead of the recessed area 24, other means may be used to ensure the accurate placement of the plate 6 within the chamber including, but not limited to, pins which cooperate with holes formed in the shelf or flanges or other projections on the surface of the shelf The recessed area 24 may be tailored to fit a specific plate configuration, with different shelves being employed for different sample plates. Alternatively, the recessed area 24 may be sized to receive the largest microwell plate with spacer templates being used to hold the smaller plates in the desired location in the recessed area.

The shelf 20 is slidably mounted to support rails 26 of the frame 18. The shelf 20 includes flanges 28 along the lateral edges of the shelf 20 which seat in grooves 30 in support rails 26. Only one support rail 26 is shown in FIG. 1, the other having been removed for clarity. The flanges 28 slide along the grooves in the support rails for the convenient removal and insertion of a plate 6 into the sample chamber. Instead of the flange/groove arrangement, it is to be understood that other means may be used to mount the shelf 20 to the frame 18. In this embodiment, the shelf 20 is manually moved into and out of the chamber, increasing the simplicity of the system 10. However, this movement may be automated if desired.

FIG. 1 shows the shelf 20 withdrawn from the chamber for positioning a microwell plate 6 on the shelf. When the shelf 20 is pushed into the chamber, the sample plate 6 is substantially aligned with the window 32 in the top plate 34 of the frame 18. As is discussed in more detail below, the mask assembly 16 extends across the window 32. The samples retained in the wells 8 of the plate 6 are read through the window 32 and the mask assembly 16.

The detection system 14 is positioned to read the samples exposed in the window. In the illustrated embodiment, the detection system 14 is a photodetection system which creates digital images of the radiant energy, including but not limited to light, alpha particles and beta particles emitted by the samples. The photodetection system utilizes a charge-coupled device (CCD) detector or camera 40 for photon counting. The CCD detector operates by converting photons striking pixels of the CCD detector into electrons, with the resulting charge of each pixel representing the number of photons striking the pixel. The received signal is stored in a computer in digital form. With the CCD detector 40, the area of the window 32 is the sample area and the CCD detector simultaneously counts the photons emitted from each of the samples exposed by the mask assembly 16. Photons emitted from each sample trigger specific pixels of the detector 40, allowing the data to be sorted by the location of the individual sample wells 8. Preferably, the CCD detector is an intensified CCD camera which amplifies the signal created by the pixels relative to background radiation and other noise to increase the sensitivity of the system such that a single photon will generate a detectable signal. A cooled CCD detector may also be employed if desired. As used herein, the term "CCD detector" includes CCD detectors, intensified CCD detectors, and cooled CCD detectors. It is to be understood that the type of detector employed depends upon the specific assay being performed. If desired, the detection system 14 may include filters to improve the clarity of detected image. For example, optical filters can be used to discriminate against different wavelengths of luminescence. The CCD detector 40 is coupled to a computer 42 which controls operation of the CCD detector. The computer also includes software for processing the stored data and generating the desired reports including for example a digital image of the light emission in two or three dimensions or a graphical representation as is known in the art.

As is shown in FIG. 1, the CCD detector is mounted to the frame 18 behind the window 32. A mirror 44 or other suitable reflecting surface is mounted above the window 32. The mirror 44 is oriented at an angle which redirects the photons emitted by the samples into the CCD detector. The angle the mirror 44 relative to the horizontal plane of the window 32 is about 40 to 50 degrees, for example 45 degrees. In other modifications of the invention, the mirror may be eliminated and the CCD detector mounted to a vertical support with the detector aimed at the window 32.

The detection system 14 of the illustrated embodiment, which includes a CCD detector, rapidly reads the samples exposed in the field of the window 32. Since both the detector and the sample tray are stationary during the operation of the detection system, the sample plate may be consistently and reliably aligned with the detector by positioning the plate 6 in the sample chamber. Complex drive mechanisms for controlling movement of these components of the system are not required. Because of these advantages, the stationary CCD detector is preferred. However, it is to be understood that other types of detection systems, such as fiber optic photodetectors which are moved relative to the wells to individually read the samples may be employed in other embodiments of the invention.

With the quantitation system 10 of this invention, all of the sample wells are not exposed through the window 32 at any given time. Instead, the mask assembly 16 exposes selected sample wells while obstructing other wells in the vicinity of the selected wells. The surface of the sample plate near the selected well is also covered, obstructing a possible source of light contamination. Covering these wells minimizes or eliminates optical crosstalk, preventing the samples in the covered wells from interfering with the accuracy of the reading of the selected sample well. In addition, the quantitation system 10 may be used to rapidly quantitate a wide range of sample intensities. As is shown particularly in FIGS. 1 and 2, the mask assembly 16 includes a plurality of apertures 50 for exposing selected sample wells. After the exposed samples have been read, other samples are exposed for quantitation by shifting the mask relative to the plate 6. This process is repeated until each of the wells 8 in a plate 6 have been exposed for analysis by the detection system 14. The number of samples around a selected sample which are covered is variable. With some assays, covering the wells immediately adjacent the selected well may provide sufficient protection against crosstalk effects. In other applications the brightness of some of the samples and the sensitivity of the assay may require covering a greater number of wells in the vicinity of the selected well. The number of apertures formed in the mask 16 is determined by the number of wells to be covered during each reading.

In the illustrated embodiment, the apertures 50 in the mask 16 are arranged in a plurality of rows 52. Solid areas 54 between adjacent rows cover alternate rows of sample wells 8 in the microwell plate 6 as is shown particularly in FIG. 2. Each row 52 of apertures includes solid areas 56 which cover alternate wells within a row of the microwell plate 6. With this configuration, all of the wells adjacent the selected sample well are covered by the mask during reading of the selected well. The wells 8 initially covered by the solid areas 54 and 56 of the mask 16 are exposed by indexing the mask relative to the sample wells. The apertures 50 of adjacent rows are staggered such that the apertures exposed by row 52a are covered by the solid areas 56 of row 52b. With the arrangement, all of the wells 8 will be exposed for quantitation by moving the mask 16 to four different positions. In the first position, shown in FIG. 3A, adjacent rows of sample wells 8 are covered by the solid areas 54. The mask 16 is indexed to the second position shown in FIG. 3B to move either row 52a or row 52b of apertures over the previously covered rows of sample wells 8. In the third position shown in FIG. 3C, the wells 8 which were covered by the mask in the first position are again covered by solid areas 54. The mask is then moved to the fourth position shown in FIG. 3D to expose selected apertures in the previously covered row by the next row of apertures 52a or 52b. Moving the mask relative to the sample plate is desirable because it avoids any sample disturbance created by moving the sample plate. However, in other embodiments of the invention, the sample plate may be moved relative to a stationary mask, or both the plate and the mask may be moved.

The aperture configuration of the illustrated embodiment is of particular advantage in that all samples adjacent the selected well are covered during reading of the selected well. By moving the mask 16 to only four positions, all of the wells in a plate 6 will be quantitated by the detection system 14. However, it is to be understood that the aperture configuration may be varied in other applications of the invention. For example, some sample media may require covering a greater number of wells near the selected well to prevent interference from cross talk.

FIG. 4 illustrates the mask 16 of the illustrated embodiment in greater detail. The mask assembly 16 includes a mask template 58 carried by a mask support 60. The mask template 58 is coupled to the support 60 by pins 62 which anchor the template 58 to the support 60. The pins 62 extend through slots 64 formed in the mask template 58 and are secured to the support, holding the template in place while permitting movement of the template relative to the pins 62. The total range of available motion is defined by the length of the slots 64. The rows 52 of the apertures discussed above, are formed in the mask template 58 and the template 58 is moved relative to the support 60 to position the rows of apertures to expose different wells 8 of the sample plate 6. The mask support 60 is formed with a plurality of apertures 66 with each of the sample wells 8 being aligned with one of the apertures in the mask support 60. The walls of the mask support 60 around the apertures 66 provide further protection against crosstalk interference. However, in other embodiments of the invention, the mask support may be formed with a window rather than a plurality of individual apertures. Moreover, instead of a mask template 58 which is movable relative to a mask support 60, the mask may be a single member which is moved relative to the frame 18.

As shown in FIGS. 1 and 2, mask assembly 16 further includes a drive system, generally designated 70, for indexing the mask template 58 relative to the mask support 60. The drive system 70 includes a pair of sprockets 72 carried by a shaft 74. The shaft 74 is coupled to a motor 76 which drives the shaft 74 to rotate the sprockets 72. The teeth 78 of the sprockets 72 engage perforations 80 (FIGS. 2 and 4) in the mask template 58 to advance the mask template 58 relative to the mask support 60. Elongated slots 82 are formed in the mask support 60 below the perforations to permit the tips of the teeth 78 to pass through the template 58 without being impeded by the mask support 60. The operation of the motor 76 is controlled by the computer 42 which controls the timing of the motor, actuating the motor 76 to rotate the sprockets to move the mask template 58 from one position to the next. In this manner, the mask template 58 is accurately and reliably moved to expose each of the sample wells 8. After the template 58 is indexed forward to the next position, the motor 76 is deactivated for a period of time for the detection system 14 to quantitate the light emitted from the exposed samples. The actual time each sample well 8 is exposed is subject to considerable variation depending upon the constraints of a particular application. After all of the sample wells have been quantitated, the motor 76 is actuated to rotate the sprockets 72 in the opposite direction to return the mask template 58 to the initial position.

Drive system 70 of the illustrated embodiment provides a convenient and efficient means of precisely controlling the movement of the mask relative to the sample wells 8. However, it is to be understood that other type of drive systems may be employed instead of the drive system 70. Moreover, drive system 70 may be modified to include a greater or lesser number of sprockets 72.

The mask template 58 and mask support 60 of the illustrated embodiment are configured for use with a microwell plate having 96 wells in an 8×12 array. However, a wide variety of plate configurations are employed in the industry, the different configurations each having a different number and/or arrangement of sample wells. The quantitation system 10 of this invention may be used with different types of sample plates 6 by replacing with mask template 58 and mask support 60 with a template and support suited for the selected sample plate. As is shown particularly in FIG. 1, the mask template and support are supported by the top plate 34 of the frame. The top plate 34 includes a recessed central section with grooves 86. The mask support 60 includes lateral flanges 88 which are slidably retained in the grooves 86 such that the mask template and mask support may be conveniently inserted into and removed from the top plate 34 of the frame. The window 32 is shaped so that the sprockets 72 are exposed through the window so that the sprocket teeth 78 may be disengaged from the perforations 80 and slots 82 before the mask support is removed from the top plate 34. Preferably, the drive system includes a lever or other suitable means (not shown) for lifting the shaft 74 and/or sprockets 72 and retaining the sprockets 72 in the disengaged position until the mask support and template have been removed and replaced from the frame 18.

In the illustrated embodiment, the quantitation system 10 is used to quantitate a plurality of samples retained within wells of a microwell plate 6. However, it is to be understood that the quantitation apparatus 10 may also be used with other devices, including samples held in petri dishes as well as gels or blots. In these applications, the mask which expose selected portions of the sample while obstructing or covering the adjacent areas of the sample. The mask is then moved to successively expose other portions of the sample until the entire sample has been exposed. Using the mask to isolate portions of the sample for a reading provides greater accuracy in measuring the light emitted from different regions of the sample.

As is apparent from the foregoing, the present invention provides a quantitation system 10 for accurately and reliably measuring the light emitted from one or more samples. The mask 16 substantially eliminates interference from crosstalk effects created by samples in the vicinity of the selected sample.

The foregoing descriptions of specific embodiments of the present invention have been presented for purposes of illustration and description. They are not intended to be exhaustive or to limit the invention to the precise forms disclosed, and obviously many modifications and variations are possible in light of the above teaching. The embodiments were chosen and described in order to best explain the principles of the invention and its practical application, to thereby enable others skilled in the art to best use the invention and various embodiments with various modifications as are suited to the particular use contemplated. It is intended that the scope of the invention be defined by the claims appended hereto and their equivalents.

What is claimed is:

1. An apparatus for reading samples carried by a sample holder, the apparatus comprising:

a detection system for reading samples;

a sample carrier support for holding a sample carrier in position for reading by the detection system;

a mask configured to expose selected portions of the sample carrier while covering other portions of the sample carrier such that said detection system reads the exposed portions of the sample carrier, said mask being movable relative to said sample carrier and said detection system to expose different portions of the sample carrier to said detection system while covering other portions of the sample carrier.

2. The apparatus of claim 1 in which said detection system is configured to measure the luminescence of the portions of the sample carrier exposed by said mask.

3. The apparatus of claim 1, and further comprising a radiation source for radiating the contents of the sample carrier such that said detection system measures fluorescence of the sample.

4. The apparatus of claim 1 in which said detection system includes a CCD detector.

5. The apparatus of claim 4 in which the detection system includes a filter between said CCD detector and said sample carrier.

6. The apparatus of claim 1 in which said sample carrier support is carried by a frame body having a window positioned to display one surface of the sample carrier to said detection system, and said mask extends across said window.

7. The apparatus of claim 1 in which the sample carrier includes a plurality of wells, said mask being configured to expose selected wells of the sample carrier and cover at least one well on each side of the selected well.

8. The apparatus of claim 1, and further comprising a sample carrier positioned on said sample support.

9. The apparatus of claim 8 in which said sample carrier is a microwell plate having a plurality of wells formed therein for holding samples.

10. An apparatus for reading samples carried by a sample holder, the apparatus comprising:

a detection system for reading samples;

a sample carrier support for holding a sample carrier in position for reading by the detection system;

a mask configured to expose selected portions of the sample carrier while covering other portions of the sample carrier such that said detection system reads the exposed portions of the sample carrier, at least one of said sample carrier and said mask being movable to expose different portions of the sample carrier to said detection system while covering other portions of the sample carrier, in which said mask includes a mask support and a mask template slidably mounted to said mask support, said mask template being movable relative to said mask support to expose different portions of the sample carrier.

11. The apparatus of claim 10 in which said mask template is opaque to substantially prevent the passage of light therethrough, said mask template having a plurality of apertures formed therethrough for exposing the portions of the sample carrier.

12. The apparatus of claim 10 in which said mask support has a plurality of apertures formed therein.

13. An apparatus for reading samples carried by a sample holder, the apparatus comprising:

a detection system for reading samples;

a sample carrier support for holding a sample carrier in position for reading by the detection system;

a mask configured to expose selected portions of the sample carrier while covering other portions of the sample carrier such that said detection system reads the exposed portions of the sample carrier, said mask being movable to expose different portions of the sample carrier to said detection system while covering other portions of the sample carrier; and an actuating device for moving said mask.

14. A sample reading apparatus comprising:

a frame body having a support member for supporting a sample carrier and a window for displaying the sample carrier;

a detection system carried by said frame body, said detection system being positioned to read the contents of the sample carrier through said window;

a mask extending across said window, said mask being configured to expose selected portions of the sample carrier and cover other portions of the sample carrier, said mask being movable to expose different portions of the sample carrier and cover other portions of the sample carrier including the previously exposed portions of the sample carrier; and an actuating system for automatically moving the mask.

15. The sample reading apparatus of claim 14 in which said detection system is configured to measure the luminescence of the samples.

16. The sample reading apparatus of claim 15, and further comprising a radiation source for radiating the contents of the sample carrier such that said detection system measures fluorescence of the sample.

17. The sample reading apparatus of claim 14 in which said detection system includes a CCD detector.

18. The sample reading apparatus of claim 14 in which said mask includes a mask support and a mask template slidably mounted to said mask support, said actuating system moving said mask template relative to said mask support to expose different portions of the sample carrier.

19. The sample reading apparatus of claim 18 in which said mask template is opaque to substantially prevent the passage of light therethrough, said mask template having a plurality of apertures formed therethrough for exposing the selected samples to said detection system.

20. The sample reading apparatus of claim 18 in which said mask support has a plurality of apertures formed therein.

21. The sample reading apparatus of claim 14 in which the sample carrier includes a plurality of wells, said mask being configured to expose selected wells of the sample carrier and cover at least one well on each side of the selected well.

22. The sample reading apparatus of claim 14, and further comprising a sample carrier supported on said support member.

23. A method of reading a sample comprising:

positioning a sample carrier on a support, obstructing a surface of the sample carrier with a mask which exposes selected portions of the sample carrier while covering other portions of the sample carrier;

activating a detection system to read the contents of the portions of the sample carrier exposed by the mask;

producing relative motion of the mask with respect to the sample carrier and the detection system to expose different portions of the sample carrier while covering other portions of the sample carrier including the previously exposed portions of the sample carrier; and activating a detection system to read the contents of the different portions of the sample carrier exposed by the mask.

24. The method of claim 23 and further comprising repeating the steps of producing relative motion of the mask and activating a detection system to read the contents of the different portions until all of the samples carried by the sample carrier have been read.

25. A method of reading a sample comprising:

positioning a sample carrier on a support, obstructing a surface of the sample carrier with a mask which exposes selected portions of the sample carrier while covering other portions of the sample carrier;

activating a detection system to read the contents of the portions of the sample carrier exposed by the mask;

producing relative motion of the sample carrier and the mask to expose different portions of the sample carrier while covering other portions of the sample carrier including the previously exposed portions of the sample carrier; and activating a detection system to read the contents of the different portions of the sample carrier exposed by the mask;

in which the step of producing relative motion of the mask and sample carrier includes moving the mask relative to the sample carrier.

26. The method of claim 25 in which the mask includes a mask support and a mask template, and the step of moving the mask includes indexing the mask template relative to the mask.

27. An apparatus for reading samples carried by a sample holder, the apparatus comprising:

a detection system for reading samples;

a sample carrier support for holding a sample carrier in position for reading by the detection system, said sample carrier including a plurality of sample wells arranged in an array;

a mask including a plurality of apertures, at least one of said sample carrier and said mask being movable relative to the other between a plurality of positions; and wherein in each said position, said mask is configured to expose a respective one of said sample wells corresponding to each of said apertures and cover all sample wells adjacent each respective sample well.

* * * * *